(12) United States Patent
Drevik et al.

(10) Patent No.: US 7,291,136 B1
(45) Date of Patent: Nov. 6, 2007

(54) ABSORBENT ARTICLE FOR USE IN A THONG GARMENT, WITH CENTRAL ADHESIVE-FREE ZONE

(75) Inventors: Solgun Drevik, Mölnlycke (SE); Anita Skeppstedt, Mölndal (SE)

(73) Assignee: SCA Hygiene Products, A.B., Gothenburg (SE)

( * ) Notice: Subject to any disclaimer, the term of this patent is extended or adjusted under 35 U.S.C. 154(b) by 364 days.

(21) Appl. No.: 10/130,353

(22) PCT Filed: Nov. 17, 2000

(86) PCT No.: PCT/SE00/02256

§ 371 (c)(1),
(2), (4) Date: May 17, 2002

(87) PCT Pub. No.: WO01/35891

PCT Pub. Date: May 25, 2001

(30) Foreign Application Priority Data

Nov. 18, 1999 (SE) .................................. 9904201

(51) Int. Cl.
*A61F 13/15* (2006.01)
(52) U.S. Cl. ........................ 604/385.03; 604/385.01; 604/386; 604/387; 604/389
(58) Field of Classification Search ........... 604/385.01, 604/385.03, 386, 389, 385.05, 387; D24/125
See application file for complete search history.

(56) References Cited

U.S. PATENT DOCUMENTS

| | | | |
|---|---|---|---|
| 5,037,417 A * | 8/1991 | Ternstrom et al. ..... | 604/385.25 |
| 5,729,835 A | 3/1998 | Williams | |
| 5,849,003 A | 12/1998 | Olsen et al. | |
| 6,059,764 A * | 5/2000 | Osborn et al. ......... | 604/385.22 |
| 6,824,535 B2 * | 11/2004 | Kolby-Falk ............ | 604/385.03 |

FOREIGN PATENT DOCUMENTS

| | | |
|---|---|---|
| EP | 0 923 921 A1 | 6/1999 |
| WO | 97/39713 | 10/1997 |
| WO | 98/33463 | 8/1998 |
| WO | 98/51249 | 11/1998 |
| WO | 00/30585 | 6/2000 |

* cited by examiner

*Primary Examiner*—Jacqueline F. Stephens
(74) *Attorney, Agent, or Firm*—Buchanan, Ingersoll & Rooney PC

(57) ABSTRACT

The invention relates to an absorbent article intended for use in a thong garment, and having a longitudinal direction and a transverse direction and comprising a liquid-permeable cover sheet (109), a liquid-tight cover sheet (110), and an absorption body (111) enclosed between the two cover sheets (109, 110), the liquid-permeable cover sheet (109) being intended to be directed towards the user's body during use and the liquid-tight cover sheet (110) being intended to be directed towards the thong garment during use, an adhesive fastening means (514, 614, 714, 814) being arranged on the liquid-tight cover sheet (110), and the article moreover having, in its longitudinal direction, a front portion (106), a rear portion (107), two side edges (102, 103), and a front edge (104) and a rear edge (105). The article has a portion which is arranged centrally between the longitudinal side edges (102, 103) and which is free of the adhesive fastening means (514, 614, 714, 814).

16 Claims, 7 Drawing Sheets

ABSORBENT ARTICLE FOR USE IN A THONG GARMENT, WITH CENTRAL ADHESIVE-FREE ZONE

TECHNICAL FIELD

The present invention relates to an absorbent article, such as a sanitary towel, a panty liner or an incontinence pad, intended for use in a thong garment, and having a longitudinal direction and a transverse direction and comprising a liquid-permeable cover sheet, a liquid-tight cover sheet, and an absorption body enclosed between the two cover sheets, the liquid-permeable cover sheet being intended to be directed towards the user's body during use and the liquid-tight cover sheet being intended to be directed towards the thong garment during use, an adhesive fastening means being arranged on the liquid-tight cover sheet, and the article moreover having, in its longitudinal direction, a front portion, a rear portion, two side edges, and a front edge and a rear edge.

BACKGROUND ART

Absorbent articles of the type mentioned at the outset are intended to be worn in close contact with the user's body. Such an absorbent article is generally placed inside the user's underwear and, during use, is held in place against the user's body by the pressure from the underwear. However, it has become increasingly common for women to wear so-called thongs, i.e. underwear with an extremely narrow crotch portion. A problem in this respect is that the sanitary towels and panty liners which have hitherto been available are shaped to fit in conventional briefs. When they are used in conjunction with thongs, a number of problems therefore arise. A practical problem is that it is virtually impossible to secure a conventional sanitary towel or panty liner in a thong garment in such a way that the towel or panty liner fits correctly in relation to the user's body and is additionally held in place throughout its use. For example, there is a very great risk of the absorbent article shifting sideways, which means that there is always a risk of leakage occurring. Another important problem is associated with the fact that thong garments are often used for aesthetic purposes since they are almost invisible, even under tight-fitting clothes, and do not give rise to unsightly edge lines or creases in the clothes.* With conventional absorbent articles which project past the edges of the thongs, much of the desired aesthetic effect of using thong garments is of course lost. A further problem which arises when using an absorbent article designed for conventional underwear is that projecting portions of the article bend and, as a result, surfaces provided with adhesive can then attach themselves to other surfaces provided with adhesive. Such adhesive-to-adhesive attachment is very difficult to break and means that it is virtually impossible to remove the article from the thongs without tearing the article.

*A conventional hour-glass shaped absorbent article is disclosed in U.S. Pat. No. 5,849,003, which article comprises adhesive fastening means.

It is therefore desirable to have an absorbent article which is adapted to the shape of a thong garment. This means that the article must be designed with a narrow rear portion and that the long sides of this rear portion are substantially arc-shaped. It is also desirable that the long sides of the article are substantially arc-shaped in order to match the shape of the thong garment. An absorbent article which satisfies the aims set out above is described in SE 9803981-1.

It is desirable that the article can be placed and secured in the thong garment in such a way in relation to the user's body that no liquid runs out past the edges of the article and that the absorption capacity of the article can be utilized to the full. Absorbent articles are generally secured in thongs with the aid of a fastening means, for example conventional fastening adhesive, friction lining or other fastening means suitable for the purpose. Swedish Patent Application 9803981-1 describes an article in which an adhesive fastening means is arranged in the form of bands extending in the longitudinal direction of the article, of which a central band of adhesive extends along a centre line extending in the longitudinal direction of the article. The adhesive fastening means is thus arranged on an area which coincides with the wetting area. Wetting area refers to the area of the liquid-permeable cover sheet which is intended to be first wetted by body fluid discharged towards the article. Such a fastening means permits very secure fastening of the absorbent article in a thong garment. However, a problem associated with the above-described positioning of the adhesive fastening means is that the absorbent article cannot move freely relative to the thong garment and therefore cannot assume the desired shape. The article according to SE 9803981-1 thus has a limited ability to adapt anatomically to the user's body, which has the consequence that the absorption capacity of the article cannot be utilized to the full.

The liquid-tight cover sheet, on the outside of which the adhesive fastening means is normally arranged, advantageously has a certain permeability to air and water vapour, which means that the absorbent article is able to breathe and thus feels comfortable to wear. Above all, it is desirable that the area of the article which, during use, coincides with the area which will be arranged over the user's genitals is not blocked against passage of air and water vapour since the area at the user's genitals is normally the area which is the most moist. A problem associated with an article according to SE 9803981-1 is that the adhesive fastening means is arranged such that it covers a large surface of the front portion of the article which, during use, substantially coincides with the user's genitals. This greatly limits the ability of the front portion to breathe, which means that the article feels damp and uncomfortable to wear.

Another problem associated with an article with adhesive fastening means arranged over a large surface of the liquid-tight cover sheet is that there is a greater risk of the thong garment, which is often made of sensitive and relatively fragile material, being damaged by the adhesive fastening means upon removal of the absorbent article from the thongs after use. A further problem associated with an article of this type is that the risk of adhesive residue remaining in the thong garment increases when the adhesive fastening means is arranged over a large surface of the liquid-tight cover sheet.

It is therefore desirable to be able to remedy the above-mentioned problems by arranging the adhesive fastening means in such a way that, during use, an optimum anatomical adaptation of the absorbent article is achieved, and at the same time the surface taken up by the adhesive fastening means is minimized.

GENERAL DISCLOSURE OF THE INVENTION

The present invention affords an absorbent article intended for use together with a thong garment, and which absorbent article substantially eliminates the problems set out above.

An article of the type mentioned at the outset, is principally characterized by the fact that the article has a portion which is arranged centrally between the longitudinal side edges and which is free of the adhesive fastening means. According to one embodiment of the invention, a band-shaped area which is free of adhesive fastening means is arranged in the transverse direction of the article. The adhesive-free area can in this case amount to at least ⅓ of the length of the article. It is also advantageous for the band-shaped area to be substantially arranged in an area which substantially coincides with the wetting area of the article. The invention thus allows the article to be placed in a satisfactory manner in relation to the user's body by means of the fact that the article in accordance with the invention has a certain degree of controlled and limited mobility and can thus follow the movement of the body, thereby affording a continuous anatomical adaptation of the article. The absorption capacity of the article can thus be utilized to the full, while at the same time considerable safety from leakage is obtained.

By arranging the adhesive fastening means slightly inside from the edges of the absorption body, the adhesive fastening means is prevented from attaching to the user's hairs and thus causing discomfort.

An adhesive fastening means arranged according to the invention is also characterized by the fact that the adhesive fastening means, at the front portion of the article, is arranged at the edges of the front portion, as a result of which the area which, during use, substantially coincides with the user's genitals is substantially free of adhesive fastening means. This means that the ability of the article to breathe is not limited, and it therefore feels comfortable to wear. It has been found to be advantageous to arrange the adhesive fastening means along the side edges of the article, at least at the front portion of the article, in such a way that the fastening means follows the contour of the side edges.

According to one embodiment of the invention, an adhesive fastening means is arranged at the rear portion of the article, along a centre line extending in the longitudinal direction of the article, in order to prevent the rear portion of the article from shifting sideways. This reduces the risk of leakage and affords optimum fastening of the panty liner in the thong garment.

It is expedient for the adhesive fastening means to be arranged over at most 30% of the surface of the article. This permits very considerable air permeability, while at the same time there is less risk of adhesive residue remaining in the thong garment, and the material of the thong garment is not damaged upon removal of the article after use.

To obtain as large an absorption surface as possible, the planar shape of the absorbent article should be adapted to the shape of the thong garment. It is therefore important that the article follows the edge of the thong garment. An absorbent article according to the invention therefore has, at least in part, substantially arc-shaped longitudinal side edges which follow the contour of the thongs in the crotch portion. In this connection, the longitudinal side edges can have different shapes, for example an undulating shape, provided the longitudinal side edges of the article have a substantial curvature in towards a centre line extending in the longitudinal direction of the article. The front edge of the article can have an arc shape which is substantially curved in an outwardly convex arc shape, seen in the longitudinal direction of the article, or can have an arc shape reminiscent of a wave with two wave crests and a wave trough, the wave trough being situated where the centre line intersects the front edge of the article. The side edges and front edge of the article can of course also have a straight shape in the transverse direction.

It has been found that the front part of most thong garments available on the market is sufficiently wide to allow the front portion of the article to be designed more freely according to the absorption capacity requirements. In order to fit in a thong garment, it has been found expedient for an article according to the invention to have a width ratio in the transverse direction of the article, between the front portion of the article and the rear portion of the article, which is from 2:1 to 4:1. In addition, an article according to the present invention should not have a length exceeding 260 mm, so that it can also fit in a thong garment with an openwork front section.

BRIEF DESCRIPTION OF THE FIGURES

The invention will now be described in greater detail with reference to the illustrative embodiments represented in the attached drawings, in which.

DETAILED DESCRIPTION OF ILLUSTRATIVE EMBODIMENTS

Figure 1:
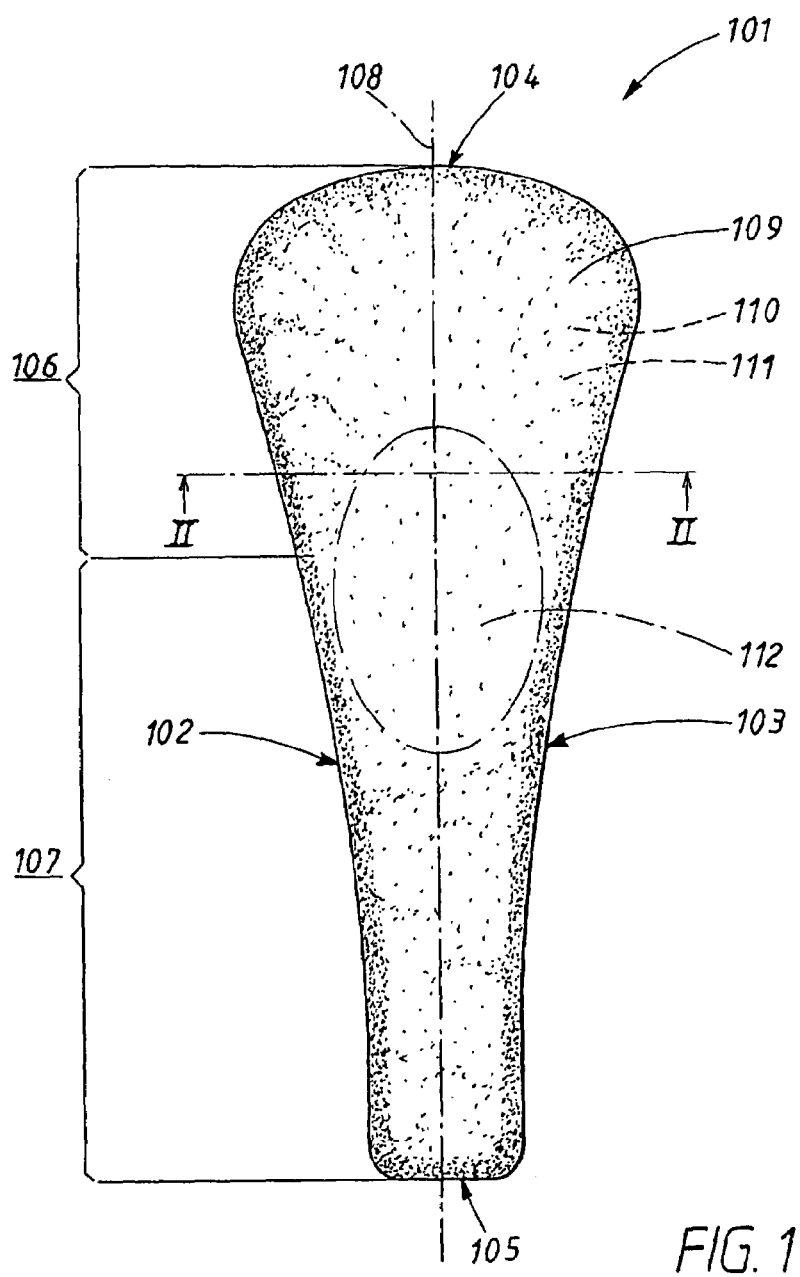
FIG. 1 shows a plan view of a panty liner, seen from the side intended to be directed towards the user when the panty liner is in use.
Figure 2:
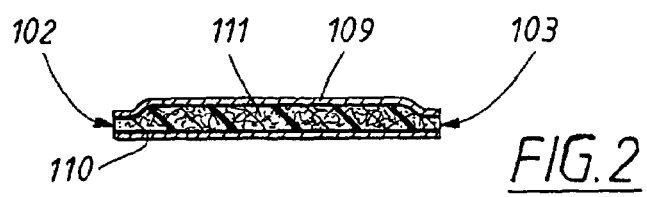
FIG. 2 shows a cross section along line II-II through the panty liner in FIG. 1.

FIGS. 1 and 2 show a panty liner 101 which has an essentially triangular shape with a longitudinal direction and a transverse direction and has two side edges 102, 103, two short sides which constitute the front edge 104 and rear edge 105 of the article, a front portion 106 and a rear portion 107, the rear portion 107 being considerably narrower than the front portion 106. The panty liner 101 also has a centre line 108 extending in the longitudinal direction. A longitudinal centre line 108 signifies a line extending along the panty liner 101 and equidistant from the side edges 102, 103 of the panty liner. The side edges 102, 103, whose principal extent is in the longitudinal direction of the panty liner, have an arc shape which is so arranged that the side edges curve in towards the longitudinal centre line 108 of the panty liner. In the rear portion 107, the side edges 102, 103 run together at the rounded rear edge 105. In the front portion 106, the side edges 102, 103 run together at the arc-shaped front edge 104. The panty liner 101 comprises a liquid-permeable cover sheet 109 arranged on that side of the panty liner 101 which during use is intended to be directed towards a user, a liquid-tight cover sheet 110 arranged on that side of the panty liner 101 which during use is intended to be directed away from the user, and an absorption body 111 enclosed between the two cover sheets 109, 110. As will be seen from FIG. 2, the liquid-permeable cover sheet 109 has essentially the same shape as the absorption body 111. At the wetting area 112 (shown by broken lines in FIG. 1), which is the portion of the panty liner 101 expected to be wetted first by most of the body fluid, the liquid-permeable cover sheet 109 can be designed with an elevation (not shown in FIG. 1). The liquid-tight cover sheet 110 is also designed like the absorption body 111. The liquid-permeable cover sheet 109, the liquid-tight cover sheet 110 and the absorption body 111 are connected to each other in a conventional manner, for example by adhesive bonding or by welding with ultrasound, connected in a seam along the edges 102, 103, 104, 105 of the panty liner.

FIG. 2 shows a cross section through the panty liner 101 along the line II-II. The liquid-permeable cover sheet 109 is of a conventional type and can thus consist of any liquid-permeable material suitable for the purpose. Examples of such materials are various types of thin nonwoven material, perforated plastic films, net material, liquid-permeable foam material or the like. The liquid-permeable cover sheet 109 can be made of two or more different materials in order to permit different functions of the cover sheet. For example, it is customary to arrange a liquid-transporting sheet inside a liquid-intake sheet. It is also known to arrange different types of material on different parts of that surface of the panty liner 101 which during use is directed towards the user. Thus, a material with good intake properties can advantageously be arranged in the wetting area, while portions of the cover sheet which are primarily intended to constitute a bearing surface against the user's body are provided with a material which has been optimized with respect to softness and comfort against the skin.

As is described in WO 98/33463, the liquid-permeable cover sheet 109 can also consist of a first sheet of conventional hydrophobic liquid-permeable material. Such materials are generally treated chemically or physically in order to create a hydrophilic wettable surface on the material. The first sheet is arranged over that surface of the absorption body 111 which is intended during use to be directed towards the user. Examples of suitable surface materials are perforated plastic films, nonwovens of hydrophobic fibres, plastic nets or the like. Such a surface material allows liquid to pass through to the absorption body 111 inside. Since the absorption body 111 is more hydrophilic than the material in the surface material, the surface material is almost completely drained of liquid. For this reason, and because the surface material has essentially no absorption capacity, the surface material remains dry even after wetting. Only a very small amount of liquid can remain on or in such a hydrophobic cover sheet.

When the panty liner 101 is in use, it is arranged in the user's genital region, with a portion situated at the user's vaginal orifice. In this way, discharged body fluid impacts the panty liner 101 within a limited surface area of the panty liner 101, the so-called wetting area. Within the wetting area, the liquid-permeable cover sheet 109 can therefore have a second hydrophilic and absorbent sheet, or can be treated so that the material within the wetting area is more hydrophilic than surrounding portions of the liquid-permeable cover sheet 109. Examples of suitable hydrophilic materials are nonwoven materials comprising rayon, cotton, cellulose fibres or the like.

It is not essential to the invention for the liquid-permeable cover sheet 109 to consist of a separate material sheet, and instead the cover sheet 109 can be a surface of the absorption body 111 of the panty liner 101. However, in such an embodiment, it is particularly expedient to provide the panty liner 101 with some form of liquid barrier which prevents liquid from being carried in the absorption material right out to the edges of the panty liner 101. Examples of such liquid barriers are compressions, welds, adhesive bands, folded-back plastic strips or hydrophobicizing means such as wax or the like.

The absorption body 111 can be an airlaid cellulose body or can be made up of any suitable absorbent material.

Other suitable absorbent materials for use in the absorption body 111 are, for example, cellulose fluff pulp, absorbent bonded fibre layers, tissue layers, absorbent foam, peat or the like. The absorption body 111 can also contain superabsorbent polymers, i.e. polymers which are able to absorb several times their own weight of liquid and form a liquid gel. Superabsorbents are generally present in the form of particles, flakes, fibres, granules or the like. The superabsorbent material can be used alone or in combination with other absorbent material.

To ensure that the panty liner, during use, does not extend so far back that it is clearly visible when used together with a thong garment, the rear portion 107, i.e. that portion of the thong garment 101 which during use is intended to be directed rearwards on the user, should expediently have a length of from 30 mm to 90 mm. The front portion 106, i.e. that portion of the panty liner 101 which during use is intended to be directed forwards on the user, should expediently have a length of 60 to 170 mm. The overall length of the article is expediently 140 to 260 mm, and preferably not more than 155 mm, so as to fit also in a thong garment with an openwork front section. The rear portion 107 and the front portion 106 do not necessarily divide the panty liner 101 into two equal parts. As will be seen from FIG. 1, the panty liner has a shape with a rounded front portion 106 which narrows towards the rear portion 107. The side edges 102, 103 of the panty liner 101 are in this case slightly curved in order to match the curvature of the leg opening of a thong garment. In the illustrative embodiment shown in FIG. 1, that area of the rear portion 107 situated nearest to the rear edge 105 has virtually straight side edges 102, 103, which means that the outermost part of the rear portion 107 has a substantially rectangular shape.

Figure 3:
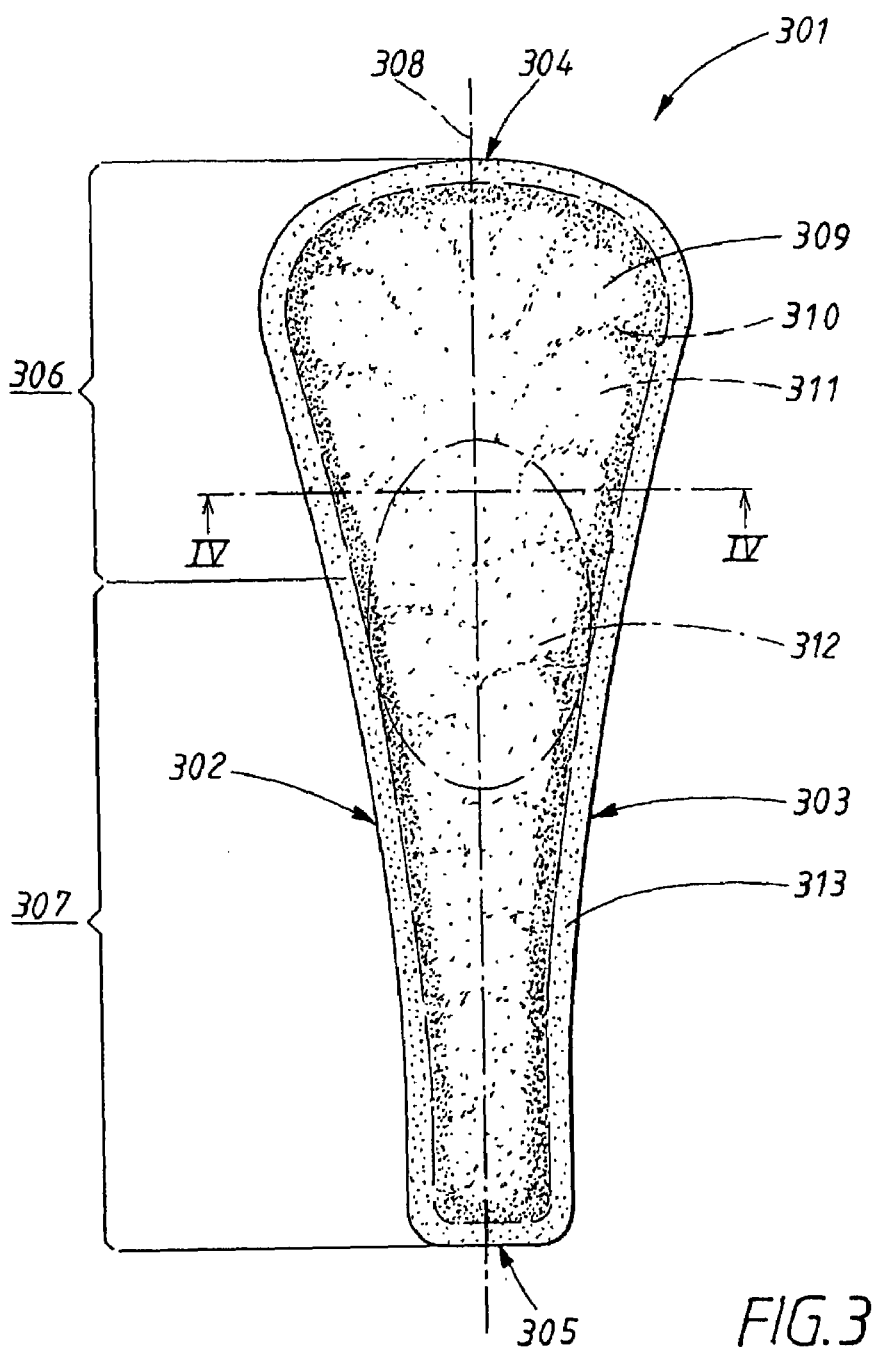
FIG. 3 shows a plan view of a panty liner, seen from the side intended to be directed towards the user when the panty liner is in use.
Figure 4:
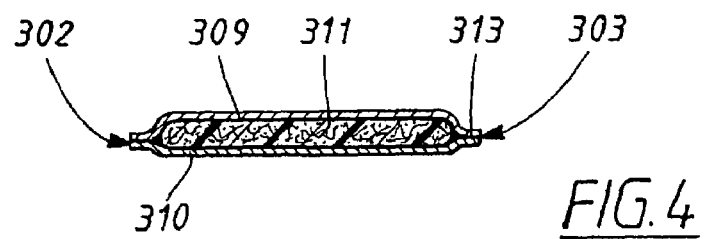
FIG. 4 shows a cross section along line IV-IV through the panty liner in FIG. 3.

FIGS. 3 and 4 show a panty liner 301 according to one embodiment of the invention. The feature distinguishing the panty liner 301 from the one described in FIGS. 1 and 2 is that the liquid-permeable cover sheet 309, which has substantially the same shape as the absorption body 311, has a slightly greater planar extent, as a result of which it forms a projecting edge 313 around the whole periphery of the absorption body 311. The liquid-tight cover sheet 310 is also shaped like the absorption body 311 and with a slightly greater planar extent than the latter. The cover sheets 309, 310 are connected to each other outside the absorption body 311, for example by adhesive bonding, stitching, or welding with heat or ultrasound.

Figure 5:
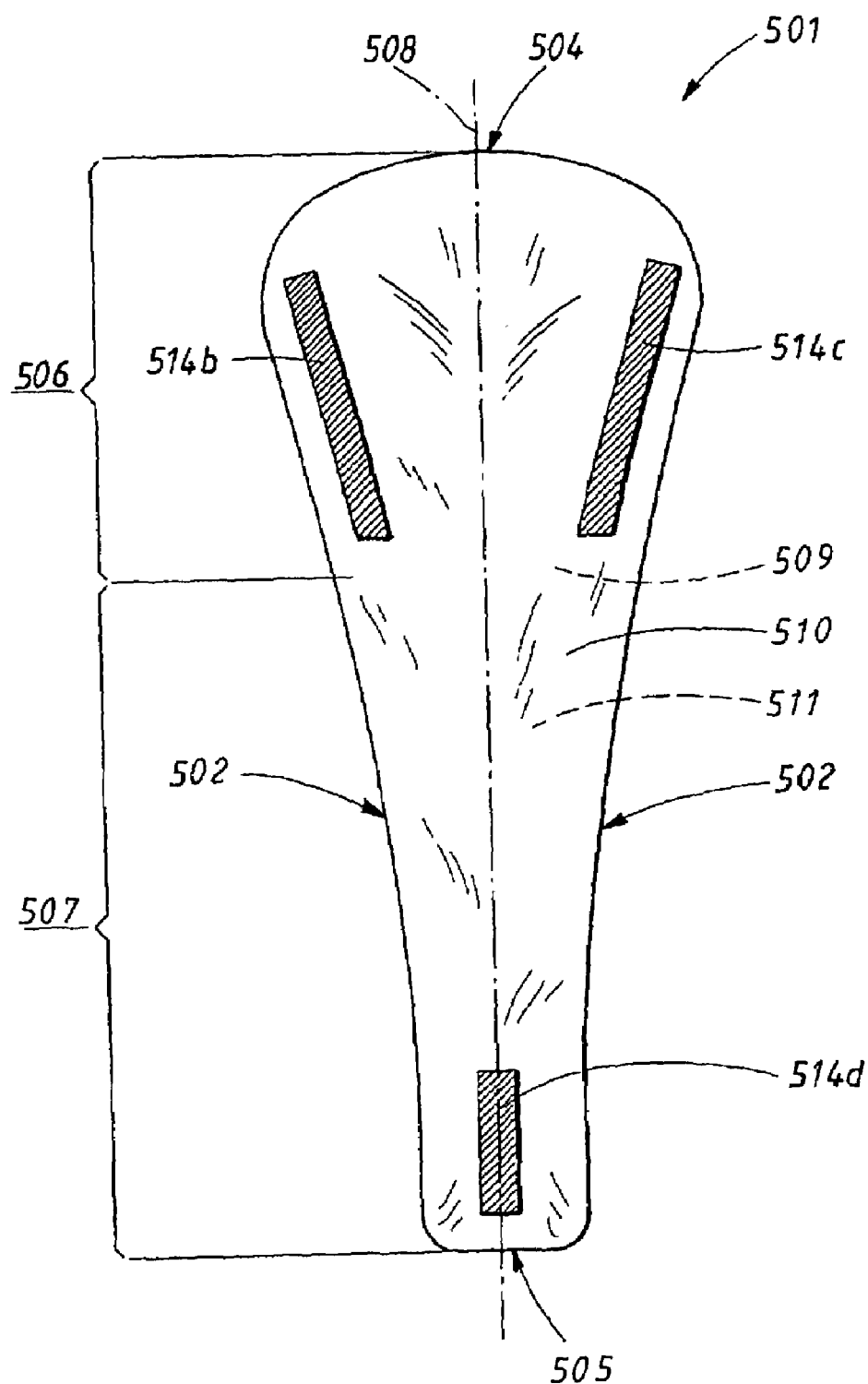
FIG. 5 shows a diagrammatic plan view of a panty liner, seen from the side intended to be directed towards the thong garment when the panty liner is in use.

FIG. 5 shows a panty liner, for example of the type which is shown in FIG. 1 or FIG. 3. FIG. 5 is a diagrammatic plan view of the panty liner 501, seen from that side which, during use of the panty liner 501, is intended to be directed towards the thong garment. When the panty liner 501 is in use, it is placed inside a thong garment and secured in the thong garment with the aid of an adhesive fastening means 514. The liquid-tight cover sheet 510 normally constitutes that side of the panty liner 501 which during use is intended to be directed towards the thong garment, and on which the adhesive fastening means 514 is arranged. As will be seen from FIG. 5, the adhesive fastening means 514 are essentially arranged close inside the edges of the absorption body 511 which, for the embodiment shown in FIG. 5, corresponds to the side edges 502, 503 of the panty liner at the front portion 506, and an area of adhesive arranged along a centre line 508 extending in the longitudinal direction of the panty liner, which area of adhesive is arranged on the outermost part of the rear portion 507 nearest the rear edge 505. Arranging the adhesive fastening means 514 inside the edges of the absorption body 511 means that user comfort is increased because there is less risk of the adhesive fastening member 514 catching on the user's hairs.

In the embodiment of the invention shown in FIG. 5, the adhesive fastening means 514 is arranged at the front portion 506 of the panty liner 101 and at the rear portion 507 of the panty liner 501. At the front portion 506, the adhesive fastening means 514 is arranged essentially at the side edges 502, 503 of the panty liner 501. The adhesive fastening means 514 is in this case arranged in two areas 514b and 514c. The areas 514b and 514c are arranged extending essentially in the longitudinal direction of the panty liner 501, along side edges 502, 503 of the panty liner, at a distance of 3 to 8 mm from the side edges 502, 503 of the panty liner 501. The areas 514b and 514c arranged in the front portion 506 both have a width which does not exceed about 39 mm and preferably does not exceed about 10 mm.

Arranged at the rear portion 507 of the panty liner 501 there is an area 514d measuring 5 to 15 mm in width and extending along the centre line 508 of the panty liner 501. The area 514d is arranged at a distance of 3 to 8 mm from the rear edge 505 of the panty liner 501. The adhesive fastening means 514 is also arranged in such a way that the areas 514b, 514c and 514d extend only so far in the longitudinal direction of the panty liner 501 as to leave a band-shaped area which extends the whole way between the side edges 502, 503 in the transverse direction of the panty liner 501 and is free of adhesive fastening means 514. It is advantageous if the band-shaped area which is arranged between the areas 514b and 514c and the area 514d constitutes at least ⅓ of the length of the panty liner 501. By arranging the adhesive fastening means 514 in the manner described above, the panty liner 501 has a portion arranged centrally between the longitudinal side edges 501, 503 and free of adhesive fastening means 514. It will also be seen from FIG. 5 that the surface of the liquid-tight cover sheet 510 on which the adhesive fastening means 514 is arranged is small. It is advantageous if the adhesive fastening means 514 is not arranged on more than 30% of the surface of the liquid-tight cover sheet 510.

Figure 6:
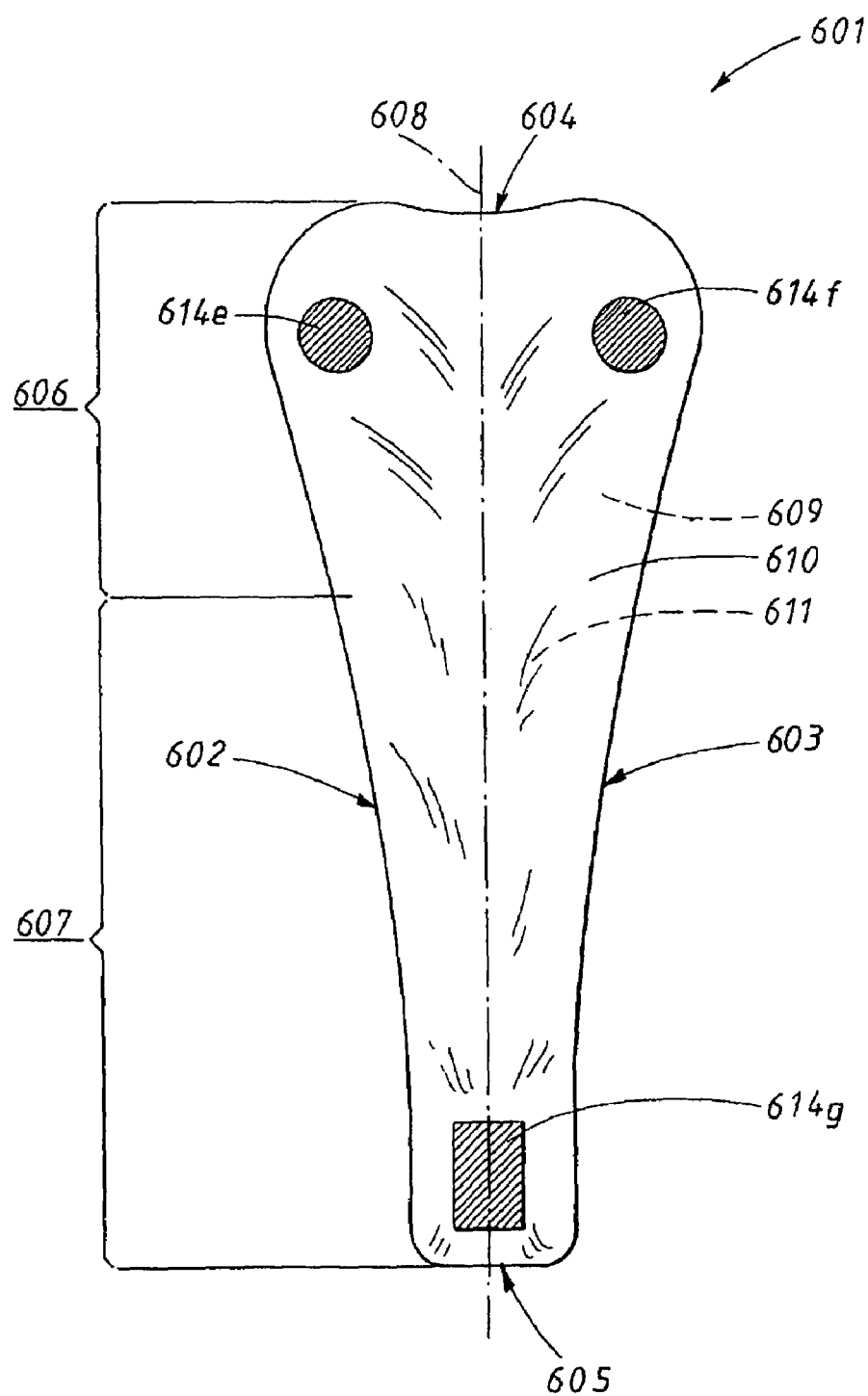
FIG. 6 shows a diagrammatic plan view of a panty liner, seen from the side intended to be directed towards the thong garment when the panty liner is in use, according to alternative embodiments of the invention.

An alternative embodiment of the invention is shown in FIG. 6. FIG. 6 is a diagrammatic plan view of a panty liner 601, seen from that side which, during use of the panty liner 601, is intended to be directed towards the thong garment. The features distinguishing the panty liner 601 in FIG. 6 from the one shown in FIG. 5 are the manner in which the adhesive fastening means 614 are arranged on the liquid-tight cover sheet 610 and the shape of the front edge 604 of the panty liner 601. It will be seen from FIG. 6 that, in the front portion 606 of the panty liner 601, fastening means 614 are arranged in two areas 614e and 614f. The areas 614e and 614f have a circular shape with a diameter of about 15 mm and are arranged at a distance of 3 to 8 mm, and preferably at a distance of 5 mm, from the side edges 602, 603 of the panty liner 601 and 3 to 8 mm, preferably 5 mm, from the front edge 604 of the panty liner 601. The front edge 604 of the panty liner 601 is curved in towards the panty liner 601 at the centre line 608, forming a "wave trough". The front edge 604 thus has a wave shape comprising two "wave crests" and one "wave trough". In addition, at the rear portion 607 of the panty liner 601 there is an area 614g which, in the same way as the area 514d, see FIG. 5, extends along the centre line 608 of the panty liner 601. The difference between the area 514d shown in FIG. 5 and the area 614g shown in FIG. 6 is that the area 614g has a slightly greater width than the area 514d. However, the area 614g is arranged such that it does not reach out to the side edges 602, 603 of the panty liner 601.

Figure 7:
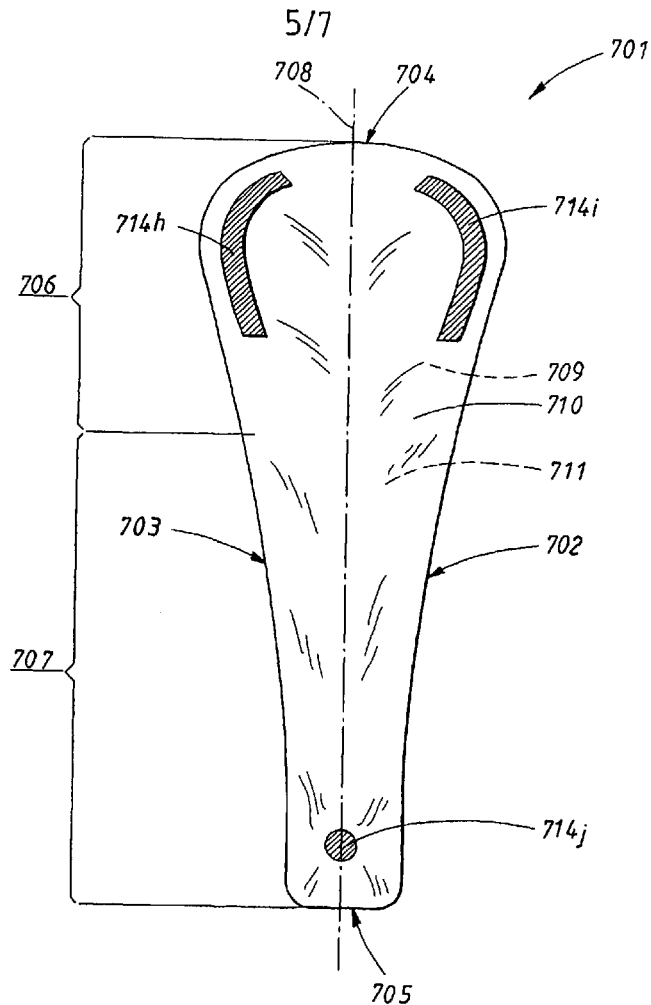
FIG. 7 shows a diagrammatic plan view of a panty liner, seen from the side intended to be directed towards the thong garment when the panty liner is in use, according to alternative embodiments of the invention.

Another alternative embodiment of the invention is shown in FIG. 7. The figure is a diagrammatic plan view of a panty liner 701, seen from that side which, during use of the panty liner 701, is intended to be directed towards the thong garment. Like the panty liner 501 shown in FIG. 5, the adhesive fastening means 714 are arranged on the liquid-tight cover sheet 710 in at least one area which is arranged inside the edges of the absorption body 711. At the front portion 706 of the panty liner 701, the adhesive fastening means 714 are arranged in two areas 714h and 714i. The areas 714h and 714i extend partially in the transverse direction of the panty liner 701 and partially in the longitudinal direction of the panty liner 701, the principal extent being in the longitudinal direction of the panty liner 701. In their extent, the areas 714h and 714i thus follow the arc shape of the side edges 702, 703 and the arc shape of the front edge 704, the areas 714h and 714i having a nonlinear shape, see FIG. 7. At the rear portion 707 of the panty liner 701, at the centre line 708 of the panty liner, there is an area 714j. The area 714j is arranged 3 to 10 mm, and preferably 5 mm, from the rear edge 705 of the panty liner 701 and has a circular shape, the diameter of the area 714j not exceeding 20 mm. The areas 714h and 714i arranged in the front portion 706 have a width which does not exceed about 30 mm and preferably does not exceed about 10 mm.

Figure 8:
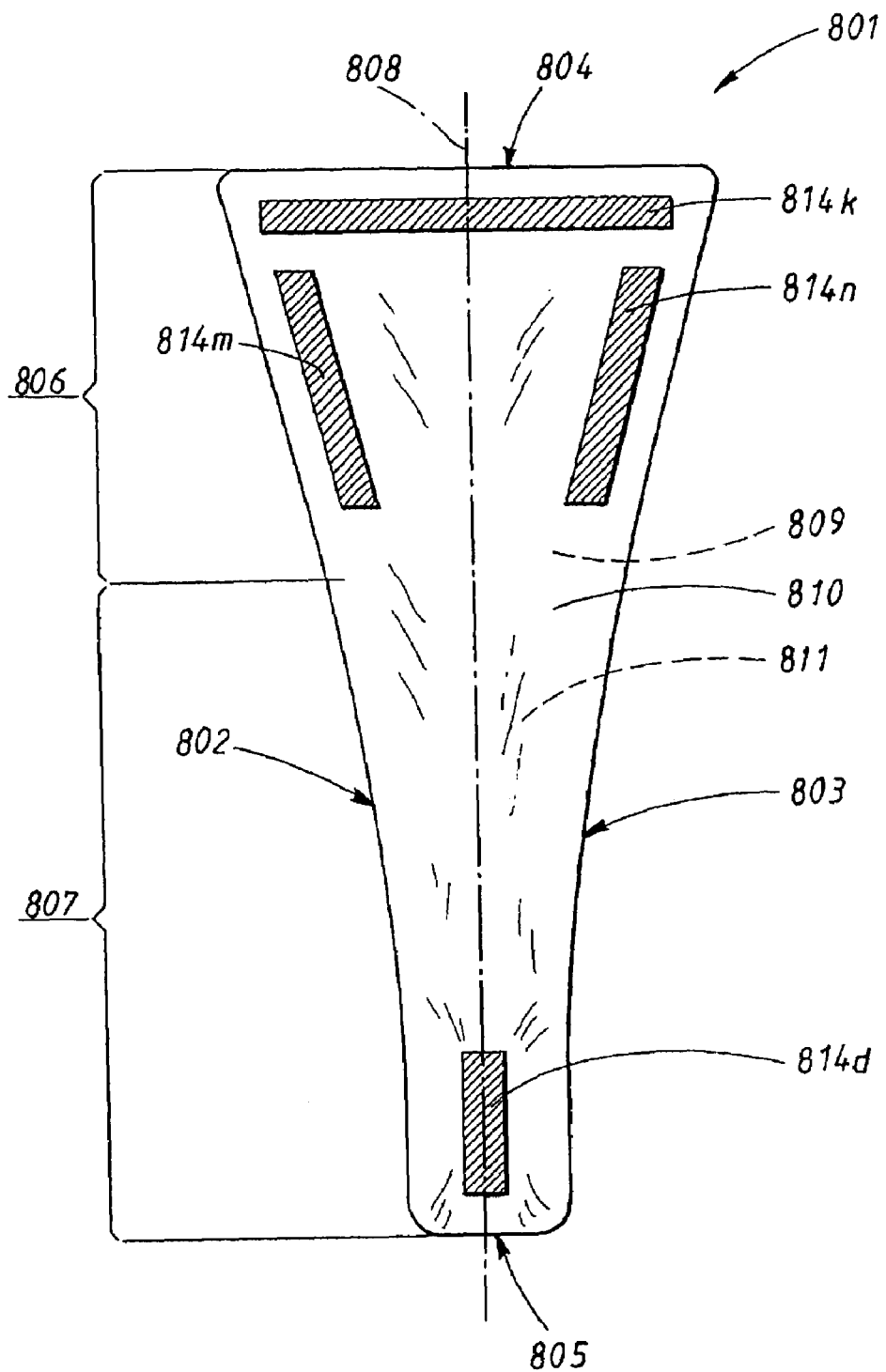
FIG. 8 shows a diagrammatic plan view of a panty liner, seen from the side intended to be directed towards the thong garment when the panty liner is in use, according to alternative embodiments of the invention.
Figure 9:
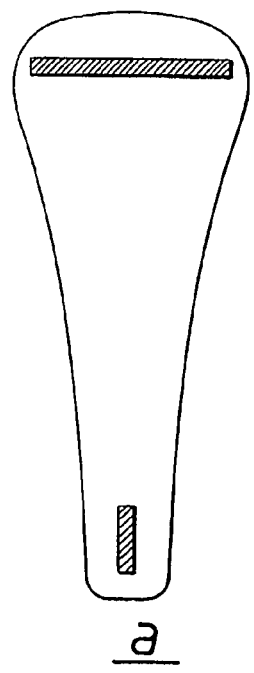
FIGS. 9a-f are diagrammatic views showing different possible positions of an adhesive fastening means according to the invention.
Figure 9:
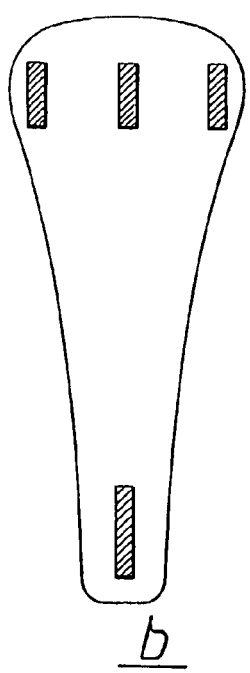
Figure 9:
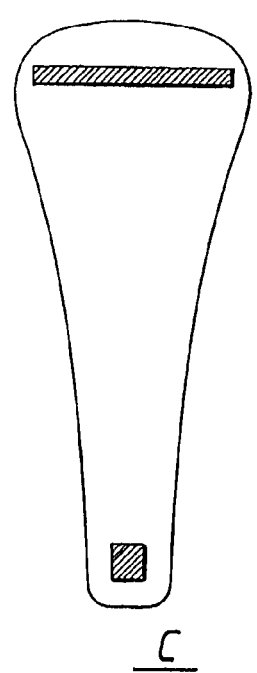
Figure 9:
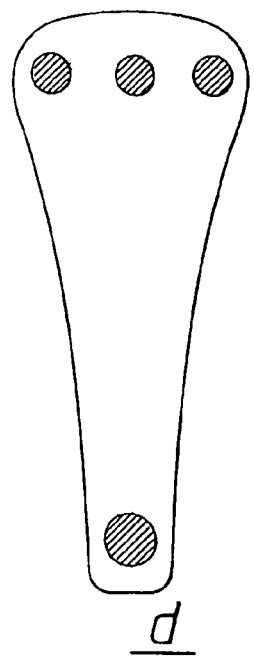
Figure 9:
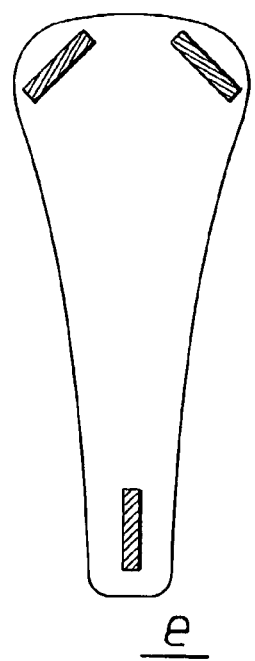
Figure 9:
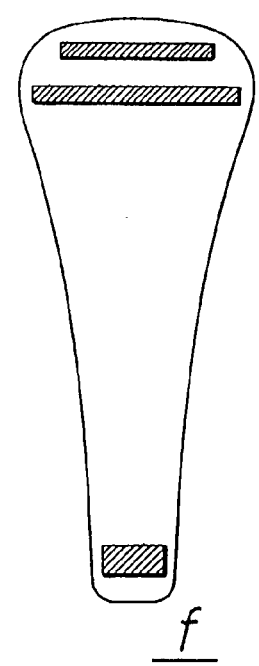

Yet another alternative embodiment of the invention is shown in FIG. 8. FIG. 8 is a diagrammatic plan view of a panty liner 801, seen from that side which, during use of the panty liner 801, is intended to be directed towards the thong garment. The adhesive fastening means 814 are arranged in four areas 814k, 814m, 814n and 814d, which are arranged in the form of straight adhesive strands along the front edge 804 and the side edges 802, 803, respectively, of the front portion 806, and in the form of a rectangular area extending along the longitudinal centre line 808 of the panty liner 801 at the rear portion 807 of the panty liner.

Like the panty liner 501 in FIG. 5, the panty liner 601 in FIG. 6, the panty liner 701 in FIG. 7 and the panty liner 801 in FIG. 8 have the adhesive fastening means 514, 614, 714, 814 arranged in such a way that a portion is obtained which is arranged centrally between the longitudinal side edges 502, 602, 702, 802; 503, 603, 703, 803 and which is free of adhesive fastening means 514, 614, 714, 814. Also, like the panty liner 501 in FIG. 5, the panty liners 601, 701, 801 in FIGS. 6, 7 and 8, respectively, have a band-shaped area in the transverse direction of the panty liner 601, 701, 801 which is free of adhesive fastening means 514, 614, 714, 814 and which constitutes at least ⅓ of the length of the panty liner 601, 701, 801.

The adhesive fastening means 514, 614, 714, 814 arranged on the liquid-tight cover sheet 510, 610, 710, 810 can consist of pressure-sensitive adhesive, velcro or any type of fastening means suitable for the purpose.

Before the panty liner 501, 601, 701, 801 is used, the adhesive fastening means 514, 614, 714, 814 is protected in a conventional manner, for example by being covered by a protective layer of paper or plastic which has been treated with silicone or embossed so as to be easily detached when the panty liner 501, 601, 701, 801 is to be used. The adhesive fastening means 514, 614, 714, 814 can of course be covered by some other suitable form of protection which is easy to detach.

As will be seen from FIGS. 9a-9f, which are all diagrammatic representations of absorbent articles seen from that side which, during use of the article, is intended to be fastened to the user's thongs and which is provided with an adhesive fastening means, the adhesive fastening means according to the invention can be arranged in a number of different ways, provided that a transverse area of the article is left free of adhesive. As has already been explained, this means that the adhesive-free area can shift slightly in relation to the thongs and thus better adapt to the user's body. It is therefore important that the article is also free of fastening adhesive at the side edges within the adhesive-free transverse area, in order to permit maximum mobility of the article, especially in a direction perpendicular to the plane of the article. In this way, the article, during use, can move in relation to the user's thongs, both laterally and vertically.

The invention must not be regarded as being limited to the above embodiments. These are merely intended to describe the invention. For example, the adhesive fastening means need not be circular, rectangular or nonlinear in shape, but can also be chosen, for example, to have an irregular shape, to be in the form of a polygon or to have an oval shape.

It is preferable for the adhesive fastening means to follow the edge lines, at least in the front portion, but it is of course also conceivable for the adhesive fastening means to be arranged otherwise within the scope of the invention.

For example, the fastening means can be arranged only at the rear portion of the article.

Features from different embodiments, in particular different parts of the adhesive patterns shown, can be combined with each other within the scope of the invention. In addition, different adhesive patterns can of course be combined with different shapes of the article. Thus, the articles which are shown in FIGS. 1, 6 and 8 have slightly different shapes in order to illustrate the possibility of variation within the scope of the invention. It is of course possible to imagine other possible alternative shapes, such as articles with a rear portion which is finished by the side edges running together at a point, heart-shaped articles, or the like. However, it is essential to the invention for the article to have such a shape as to fit into a thong garment. This means that an article according to the invention must have a very narrow rear portion and a relatively wide front portion.

Although the invention has been described in connection with a panty liner, it is of course also possible to apply the invention to a sanitary towel or an incontinence pad.

The invention claimed is:

1. Absorbent article intended for use in a thong garment, and having a longitudinal direction and a transverse direction, the absorbent article comprising:
    a liquid-permeable cover sheet, a liquid-tight cover sheet, and an absorption body enclosed between the two cover sheets, the liquid-permeable cover sheet being intended to be directed towards a user's body during use and the liquid-tight cover sheet being intended to be directed towards the thong garment during use,
    an adhesive fastening means being arranged on the liquid-tight cover sheet,
    wherein the absorbent article has an essentially triangular shape including, in its longitudinal direction, a front portion, a rear portion, two longitudinal side edges, and a front edge and a rear edge,
    wherein the absorbent article has a portion which is arranged centrally between the longitudinal side edges and which is free of the adhesive fastening means,
    wherein in the transverse direction of the article, there is a continuous area extending between the longitudinal side edges, covering an entire distance between the side edges and free of adhesive fastening means, wherein the extent of the continuous area in the longitudinal direction of the article constitutes at least ⅓ of the length of the article, and
    wherein the rear portion of the article has a width not exceeding 40 mm,
    wherein the width ratio in the transverse direction between the front portion of the article and the rear portion of the article is from 2:1 to 4:1, whereby the absorbent article defines an essentially triangular shape when in use that is dimensioned for placement substantially within a perimeter of the thong garment.

2. The absorbent article according to claim 1, wherein the adhesive fastening means is arranged over at most 30% of the surface of the liquid-tight cover sheet.

3. The absorbent article according to claim 1, wherein the adhesive fastening means is arranged at a distance from the edges of the absorption body.

4. The absorbent article according to claim 1, wherein the adhesive fastening means is arranged at the front portion of the article.

5. The absorbent article according to claim 1, wherein the adhesive fastening means is arranged at the front portion of the article and at the rear portion of the article.

6. The absorbent article according to claim 1, wherein the adhesive fastening means is arranged along the longitudinal side edges of the article, at least at the front portion of the article and thus follows the contour of the side edges.

7. The absorbent article according to claim 1, wherein the adhesive fastening means at the rear portion of the article is arranged along a center line extending in the longitudinal direction of the article.

8. The absorbent article according to claim 1, wherein the side edges of the article are curved in towards a center line extending in the longitudinal direction of the article.

9. The absorbent article according to claim 1, wherein the front edge of the article is substantially curved in an arc shape.

10. The absorbent article according to claim 1, wherein the whole length of the article does not exceed 260 mm.

11. The absorbent article according to claim 10, wherein the whole length of the article does not exceed 155 mm.

12. The absorbent article according to claim 1, wherein said adhesive fastening means includes a front adhesive fastening means and a rear adhesive fastening means, said front and rear adhesive fastening means being arranged for attachment to a user-facing side of the thong garment during use.

13. The absorbent article according to claim 1, wherein the liquid-permeable cover sheet and the liquid-tight cover sheet have essentially the same shape as the absorption body.

14. The absorbent article according to claim 1, wherein a contour of the absorbent article follows a contour of the thong garment.

15. Absorbent article intended for use in a thong garment, and having a longitudinal direction and a transverse direction, the absorbent article comprising:
- a liquid-permeable cover sheet, a liquid-tight cover sheet, and an absorption body enclosed between the two cover sheets, the liquid-permeable cover sheet being intended to be directed towards a user's body during use and the liquid-tight cover sheet being intended to be directed towards the thong garment during use,
- an adhesive fastening means being arranged on the liquid-tight cover sheet,
- wherein the absorbent article has an essentially triangular shape including, in its longitudinal direction, a front portion, a rear portion, two longitudinal side edges, and a front edge and a rear edge, the absorbent article defining a shape configured for placement in a thong garment,
- wherein the absorbent article has a portion which is arranged centrally between the longitudinal side edges and which is free of the adhesive fastening means,
- wherein in the transverse direction of the article, there is a continuous area extending between the side edges, covering an entire distance between the side edges and free of adhesive fastening means, wherein the extent of the continuous area in the longitudinal direction of the article constitutes at least ⅓ of the length of the article, and
- wherein the adhesive fastening means is arranged along the longitudinal side edges of the article, at least at the front portion of the article and thus follows the contour of the side edges,
- wherein the liquid-permeable cover sheet and the liquid-tight cover sheet have essentially the same shape as the absorption body, the liquid-permeable cover sheet, the liquid-tight cover sheet and the absorption body have an essentially triangular shape when in use that is dimensioned for placement substantially within a perimeter of the thong garment.

16. The absorbent article according to claim 15, wherein said adhesive fastening means includes a front adhesive fastening means and a rear adhesive fastening means, said front and rear adhesive fastening means being arranged for attachment to a user-facing side of the thong garment during use.

* * * * *